United States Patent
Kleckner et al.

(10) Patent No.: US 7,233,824 B2
(45) Date of Patent: Jun. 19, 2007

(54) SECURE AND EFFICACIOUS THERAPY DELIVERY FOR AN EXTRA-SYSTOLIC STIMULATION PACING ENGINE

(75) Inventors: Karen J. Kleckner, New Brighton, MN (US); Kathleen A. Prieve, Shoreview, MN (US); Jeffrey M. Gillberg, Coon Rapids, MN (US); Ren Zhou, Blaine, MN (US); Kenneth M. Anderson, Bloomington, MN (US); D. Curtis Deno, Andover, MN (US); Glenn C. Zillmer, Hudson, WI (US); Ruth N. Klepfer, St. Louis Park, MN (US); Vincent E. Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 521 days.

(21) Appl. No.: 10/703,956

(22) Filed: Nov. 7, 2003

(65) Prior Publication Data

US 2005/0101998 A1 May 12, 2005

Related U.S. Application Data

(60) Provisional application No. 60/509,335, filed on Oct. 7, 2003.

(51) Int. Cl.
*A61N 1/365* (2006.01)
*A61N 1/368* (2006.01)

(52) U.S. Cl. .............................. 607/11; 607/9; 607/14; 607/15

(58) Field of Classification Search .................... 607/9, 607/11, 14, 15
See application file for complete search history.

(56) References Cited

U.S. PATENT DOCUMENTS

| 5,117,824 A | 6/1992 | Keimel et al. |
| 5,213,098 A | 5/1993 | Bennett et al. |
| 6,438,408 B1 * | 8/2002 | Mulligan et al. ........... 600/510 |
| 2002/0147468 A1 | 10/2002 | Kim et al. |
| 2003/0032986 A1 | 2/2003 | Kupper |
| 2005/0090872 A1 * | 4/2005 | Deno et al. ................... 607/25 |

FOREIGN PATENT DOCUMENTS

| EP | 0 494 487 A2 | 7/1992 |
| WO | WO 01/58518 | 8/2002 |
| WO | WO 02/053026 | 11/2002 |
| WO | WO 03/020364 A2 | 3/2003 |

* cited by examiner

*Primary Examiner*—Carl Layno
*Assistant Examiner*—Tammie K. Heller
(74) *Attorney, Agent, or Firm*—Paul H. McDowall; Girma Wolde-Michael

(57) ABSTRACT

An extra-systolic stimulation (ESS) therapy addresses cardiac dysfunction including heart failure. ESS therapy employs atrial and/or ventricular extra-systoles via pacing-level stimulation to a heart. These extra-systoles must be timed correctly to achieve beneficial effects on myocardial mechanics (efficacy) while maintaining an extremely low level of risk of arrhythmia induction and excellent ICD-like arrhythmia sensing and detection (security). The present invention relates to therapy delivery guidance and options for improved ESS therapy delivery. These methods may be employed individually or in combinations in an external or implantable ESS therapy delivery device.

17 Claims, 11 Drawing Sheets

SECURE AND EFFICACIOUS THERAPY DELIVERY FOR AN EXTRA-SYSTOLIC STIMULATION PACING ENGINE

CROSS REFERENCE TO RELATED APPLICATIONS

The present non-provisional patent application claims the benefit of provisional patent application Ser. No. 60/509,335 entitled, "SECURE AND EFFICACIOUS THERAPY DELIVERY FOR AN EXTRA-SYSTOLIC STIMULATION PACING ENGINE," filed 7 Oct. 2003 and hereby cross-references and incorporates by reference the entire contents of the following applications, each of which is filed on 7 Oct. 2003: non-provisional U.S. application Ser. No. 10/680,528 entitled, "REFRACTORY PERIOD TRACKING AND ARRHYTHMIA DETECTION," non-provisional U.S. application Ser. No. 10/680,462, entitled, "METHOD AND APPARATUS FOR CONTROLLING EXTRA-SYSTOLIC STIMULATION (ESS) THERAPY USING ISCHEMIA DETECTION," non-provisional U.S. application Ser. No. 10/680,494 entitled, "METHOD AND APPARATUS FOR OPTIMIZATION AND ASSESSMENT OF RESPONSE TO EXTRA-SYSTOLIC STIMULATION (ESS) THERAPY," non-provisional U.S. application Ser. No. 10/680,493 entitled, "EXTRA-SYSTOLIC STIMULATION THERAPY DELIVERY AND SENSING VIA DIFFERENT ELECTRODE SETS," non-provisional U.S. application Ser. No. 10/680,695 entitled, "MULTIPLE PACING OUTPUT CHANNELS," and non-provisional U.S. application Ser. No. 10/692,990, now U.S. Pat. No. 7,142,916 entitled, "CARDIAC PACING MODALITY HAVING IMPROVED BLANKING, TIMING, AND THERAPY DELIVERY METHODS FOR EXTRA-SYSTOLIC STIMULATION PACING THERAPY."

FIELD OF THE INVENTION

The present invention relates generally to the field of cardiac stimulation devices and more specifically to a device and method for secure and efficacious delivery of an extra-systolic stimulation (ESS) therapy to improve hemodynamic function in the treatment of cardiac mechanical insufficiency. In particular, implantable and external devices device and methods of therapy delivery according to the present invention are provided for adjusting the timing and delivery of extra-systolic stimulation.

BACKGROUND OF THE INVENTION

Cardiac myocytes stimulated with so-called paired, coupled, bi-geminal or intercalated pacing stimulation produce enhanced mechanical function on subsequent depolarizations of the heart. Herein, this type of cardiac pacing therapy is referred to as extra-systolic stimulation (ESS) which refers to delivery of cardiac pacing therapy soon after either an intrinsic or pacing-induced systole. The magnitude of the enhanced mechanical function is strongly dependent on the timing of the extra systole relative to the preceding intrinsic or paced systole. When correctly timed, an ESS pulse causes depolarization of the heart but the attendant mechanical contraction is absent or substantially weakened. The contractility of the subsequent cardiac cycles, referred to as the post-extra-systolic beats, is increased as described in detail in commonly assigned U.S. Pat. No. 5,213,098 issued to Bennett et al., incorporated herein by reference in its entirety.

The mechanism of ESS is thought to be related to the calcium cycling within the myocytes. The extra systole initiates a limited calcium release from the sarcolasmic reticulum (SR). The limited amount of calcium that is released in response to the extra systole is not enough to cause a normal mechanical contraction of the heart. After the extra systole, the SR continues to take up calcium with the result that subsequent depolarization(s) cause a large release of calcium from the SR, resulting in vigorous myocyte contraction.

As noted, the degree of mechanical augmentation on post-extra-systolic beats depends strongly on the timing of the extra systole following a first depolarization, referred to as the extra-systolic interval (ESI). If the ESI is too long, the ESS effects are not achieved because a normal mechanical contraction takes place in response to the extra-systolic stimulus. As the ESI is shortened, a maximal effect is reached when the ESI is slightly longer than the physiologic refractory period. An electrical depolarization occurs without a mechanical contraction or with a substantially weakened contraction. When the ESI becomes too short, the stimulus falls within the absolute refractory period and no depolarization occurs.

The above-cited Bennett patent generally discloses a post-extra-systolic potentiation stimulator for the treatment of congestive heart failure or other cardiac dysfunctions. A cardiac performance index is developed from a sensor employed to monitor the performance of the heart, and a cardiac stress index is developed from a sensor employed to monitor the cardiac muscle stress. Either or both the cardiac performance index and cardiac stress index may be used in controlling the delivery of ESS stimulation. Prior non-provisional U.S. patent application Ser. No. 10/322,792 filed 28 Aug. 2002 and corresponding PCT application (publication no. WO 02/053026) by to Deno et al., which is hereby incorporated herein by reference in its entirety, discloses an implantable medical device for delivering post extra-systolic potentiation stimulation. ESS stimulation is employed to strengthen the cardiac contraction when one or more parameters indicative of the state of heart failure show that the heart condition has progressed to benefit from increased contractility, decreased relaxation time, and increased cardiac output. PCT Publication WO 01/58518 issued to Darwish et al., incorporated herein by reference in its entirety, generally discloses an electrical cardiac stimulator for improving the performance of the heart by applying paired pulses to a plurality of ventricular sites. Multi-site paired pacing is proposed to increase stroke work without increasing oxygen consumption and, by synchronizing the timing of the electrical activity at a plurality of sites in the heart, decrease a likelihood of development of arrhythmia.

As indicated in the referenced '098 patent, one risk associated with ESS stimulation is arrhythmia induction. If the extra-systolic pulse is delivered to cardiac cells during the vulnerable period, the risk of inducing tachycardia or fibrillation in arrhythmia-prone patients is higher. The vulnerable period encompasses the repolarization phase of the action potential, also referred to herein as the "recovery phase" and a period immediately following it. During the vulnerable period, the cardiac cell membrane is transiently hyper-excitable. Therefore, although the property of ESS has been known of for decades, the application of ESS in a cardiac stimulation therapy for improving the mechanical function of the heart has not been realized clinically because of the perceived risks.

In delivering extra-systolic stimulation for achieving mechanical enhancement of cardiac function on post-extrasystolic beats, therefore, it is important to avoid certain extra-systolic intervals that under certain circumstances, may cause arrhythmias or other deleterious effects. When securely delivered, the mechanical effects of ESS therapy may advantageously benefit a large number of patients suffering from cardiac mechanical insufficiency, such as patients in heart failure, among others. Hence, a method for secure and effective control of ESS therapy is needed that provides all the advantages with little or no of the potential disadvantages.

SUMMARY OF THE INVENTION

Extra-systolic stimulation (ESS) therapy is a means to treat cardiac dysfunction including heart failure that employs atrial and/or ventricular extra-systoles via pacing like stimulation of the heart. These extra-systoles must be timed correctly to achieve beneficial effects on myocardial mechanics (benefit) while maintaining an extremely low level of risk of arrhythmia induction and excellent ICD-like arrhythmia sensing and detection (security). This timing must adapt to variations in refractory period such as those resulting from intrinsic or physiologic rate changes and not compromise security or benefit. Further experience with ESS has led to improved implementation methods that depend on better blanking, ESS stimulation timing, and ESS delivery rules. These methods may be employed individually or in combinations in an external or implantable ESS device. A list of these improvements appears below:

The present invention pertains to a series of therapy delivery security options for the secure delivery of an ESS therapy. In one form of the present invention, the inventive therapy delivery options involve monitoring cardiac activity on a cycle-by-cycle basis during delivery of ESS therapy and based on the monitored activity determining whether or not ESS therapy delivery should commence and/or continue.

For example, therapy delivery could be inhibited in the event that a premature beat (or depolarization) occurs such as a premature atrial contraction (PAC) or a premature ventricular contraction (PVC).

In addition, the present invention maintains adequate arrhythmia detection and in the event that detection occurs, delivery of an ESS therapy is inhibited. Maintaining robust detection of ventricular tachycardia (VT) and ventricular fibrillation (VF) is deemed a prerequisite for secure and efficacious delivery of an ESS therapy.

Representative rules according to the present invention include

Delivery of an ESS therapy only at pacing rates (pacing per minute or PPM) and a corresponding heart rate (HR) range to enhance efficacy of the therapy.

Inhibit delivery of an ESS therapy in the event that a PVC occurs on a preceding cardiac cycle.

Ensure that the relatively short extra-systolic interval (ESI) typical of an ESS therapy do not inappropriately bias arrhythmia detection algorithms toward erroneous VT/VF detection.

Maintain adequate VT/VF detection in the presence of the additional blanking periods typically imposed during delivery of an ESS therapy.

Withhold delivery of an ESS therapy during VT/VF episodes.

Avoid potential under-sensing of VT by withholding delivery of an ESS therapy in the event that an evidence counting-type VT detection algorithm has reached a threshold (prior to declaring positive detection of VT).

Maintain the ability to mode switch in the presence of a detected atrial tachycardia (AT) and suspend delivery of an ESS therapy or mode switch to a ventricular coupled pacing (VCP) modality in the event that an AT episode is detected.

Discontinue ESS therapy delivery if a tachycardia episode emerges during ESS therapy delivery and only commence ESS therapy delivery following clinician intervention (e.g., remote or in-person device interrogation).

Accordingly, the present invention provides a system and method for securely controlling the delivery of ESS therapy to effectively produce augmented stroke volume and cardiac output in the treatment of cardiac mechanical insufficiency.

According to one form of the present invention, ESS therapy delivery is controlled based on security rules that are preferably applied on a cycle-to-cycle basis. As such, the system includes an implantable medical device and associated lead system for delivering electrical stimulation pulses to the heart and receiving and processing electrical cardiac signals from the heart. The system includes arrhythmia detection and pacing therapy delivery capabilities and optionally, cardioversion and defibrillation capabilities. In some embodiments, the system further includes one or more physiological sensors for measuring cardiac hemodynamic or contractile function in order to assess the strength of the myocardial contraction during extra systoles and/or during depolarizations subsequent to delivery of ESS therapy.

DETAILED DESCRIPTION OF THE INVENTION

The present invention is generally directed toward providing an implantable system for delivering an electrical stimulation therapy to achieve augmented stroke volume (and, under certain conditions, cardiac output) by providing a carefully timed pacing stimulus to a chamber of a heart following an intrinsic or evoked depolarization. Herein the therapy is referred to herein as extra-systolic stimulation (ESS).

The timing of ESS therapy results in the device giving the patient a pacing stimulus relatively close to what has historically been called the "vulnerable zone." The general consensus is that during the first few milliseconds after the refractory period—and depending to a degree on the magnitude of the ESS pulse delivered—the heart may have an increased vulnerability to a tachyarrhythmia and the risk of inducing a VT or VF with a pacing stimulus may be increased during this time.

The fact that ESS therapy pulses can be delivered at typical pacing amplitudes greatly reduces the arrhythmia risk. Adaptive timing is also being explored to position the ESS therapy pulses some distance from the peak of the vulnerable zone. The purpose of the security rules discussed in this paper is to decide on a cycle-by-cycle basis whether or not to deliver ESS therapy. The security rules: 1) deliver ESS therapy only at rates low enough that efficacy can be ensured, 2) not deliver ESS therapy coupled to premature ventricular beats, 3) ensure that the short intervals associated with ESS therapy do not inappropriately bias detection algorithms towards VT/VF detection, 4) maintain adequate VT/VF detection in the presence of the additional blanking imposed by ESS therapy delivery, 5) allow for potential undersensing of a ventricular tachyarrhythmia, 6) maintain the ability to mode switch in the presence of an atrial tachyarrhythmia (and suspend ESS therapy or switch to Vcp only delivery if mode switch occurs), and 7) allow ESS therapy to be suspended if one or more ventricular tachyarrhythmias occur.

Figure 1A:
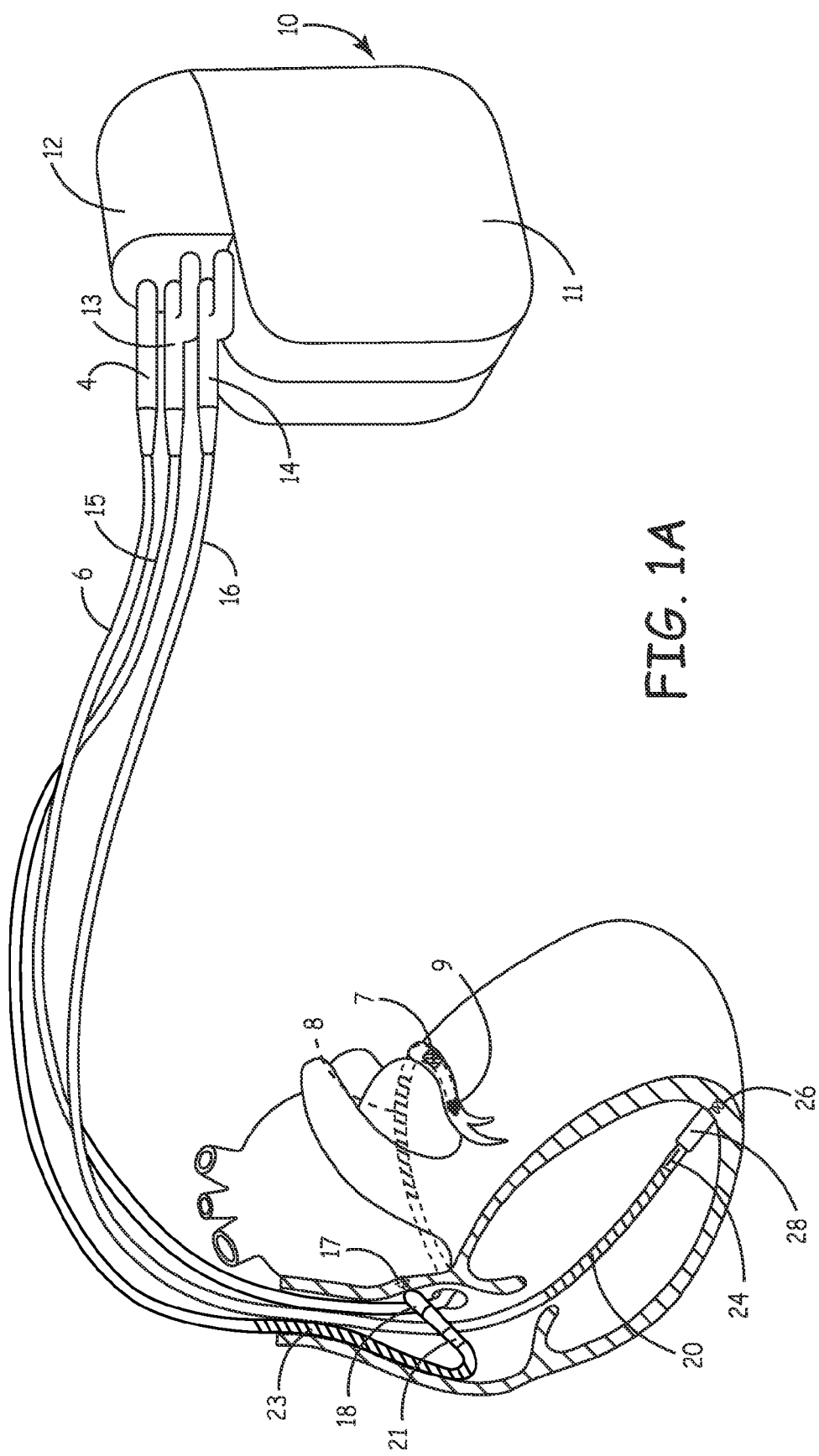
FIG. 1A is an illustration of an exemplary implantable medical device (IMD) in which the present invention may be implemented.

FIG. 1A is an illustration of an exemplary implantable medical device (IMD) in which the present invention may be implemented. IMD 10 is coupled to a patient's heart by three cardiac leads 6,15,16. IMD 10 is capable of receiving and processing cardiac electrical signals and delivering electrical stimulation pulses for ESS and may additionally be capable of cardiac pacing, cardioversion and defibrillation. IMD 10 includes a connector block 12 for receiving the proximal end of a right ventricular lead 16, a right atrial lead 15 and a coronary sinus lead 6, used for positioning electrodes for sensing and stimulating in three or four heart chambers.

In FIG. 1A, the right ventricular lead 16 is positioned such that its distal end is in the right ventricle for sensing right ventricular cardiac signals and delivering electrical stimulation therapies in the right ventricle which includes at least ESS and may include cardiac bradycardia pacing, cardiac resynchronization therapy, cardioversion and/or defibrillation. For these purposes, right ventricular lead 16 is equipped with a ring electrode 24, a tip electrode 26 optionally mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to IMD 10.

The right atrial lead 15 is positioned such that its distal end is in the vicinity of the right atrium and the superior vena cava. Lead 15 is equipped with a ring electrode 21, a tip electrode 17, optionally mounted retractably within electrode head 19, and a coil electrode 23 for providing sensing and electrical stimulation therapies in the right atrium, which may include atrial ESS and/or other cardiac pacing therapies, cardioversion and/or defibrillation therapies. In one application of ESS, ESS is delivered to the atria to improve the atrial contribution to ventricular filling. The extra-systolic depolarization resulting from the atrial ESS stimulation pulse may be conducted to the ventricles for achieving ESS effects in both the atrial and ventricular chambers. The ring electrode 21, the tip electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1A as having a defibrillation coil electrode 8 that may be used in combination with either the coil electrode 20 or the coil electrode 23 for delivering electrical shocks for cardioversion and defibrillation therapies. Coronary sinus lead 6 is also equipped with a distal tip electrode 9 and ring electrode 7 for sensing functions and delivering ESS in the left ventricle of the heart as well as other cardiac pacing therapies. The coil electrode 8, tip electrode 9 and ring electrode 7 are each coupled to insulated conductors within the body of lead 6, which provides connection to the proximal bifurcated connector 4. In alternative embodiments, lead 6 may additionally include ring electrodes positioned for left atrial sensing and stimulation functions, which may include atrial ESS and/or other cardiac pacing therapies.

The electrodes 17 and 21, 24 and 26, and 7 and 9 may be used in sensing and stimulation as bipolar pairs, commonly referred to as a "tip-to-ring" configuration, or individually in a unipolar configuration with the device housing 11 serving as the indifferent electrode, commonly referred to as the "can" or "case" electrode. IMD 10 is preferably capable of delivering high-voltage cardioversion and defibrillation therapies. As such, device housing 11 may also serve as a subcutaneous defibrillation electrode in combination with one or more of the defibrillation coil electrodes 8, 20 or 23 for defibrillation of the atria or ventricles.

For the purposes of delivering ESS therapy in accordance with the present invention, for at least one cardiac cycle during such therapy delivery various timing intervals or parameters are monitored. For example, a ventricular and/or atrial electrogram (EGM) may be derived by monitoring a bipolar "tip-to-ring" sensing vector, a unipolar tip-to-can sensing vector, a unipolar tip-to-coil or ring-to-coil sensing vector, or a relatively more global coil-to-can sensing vector.

It is recognized that alternate lead systems may be substituted for the three lead system illustrated in FIG. 1A. For example, lead systems including one or more unipolar, bipolar and/or mulitpolar leads may be configured for sensing cardiac electrical signals and/or delivering an ESS therapy according to the present invention. It is contemplated that extra-systolic stimuli may be delivered at one or more sites within the heart. Accordingly, lead systems may be adapted for sensing cardiac electrical signals at multiple cardiac sites and for delivering extra-systolic stimuli at the multiple sites, which may be located in one or more heart chambers. It is further contemplated that subcutanteous ECG electrodes could be included in the implantable system.

Figure 1B:
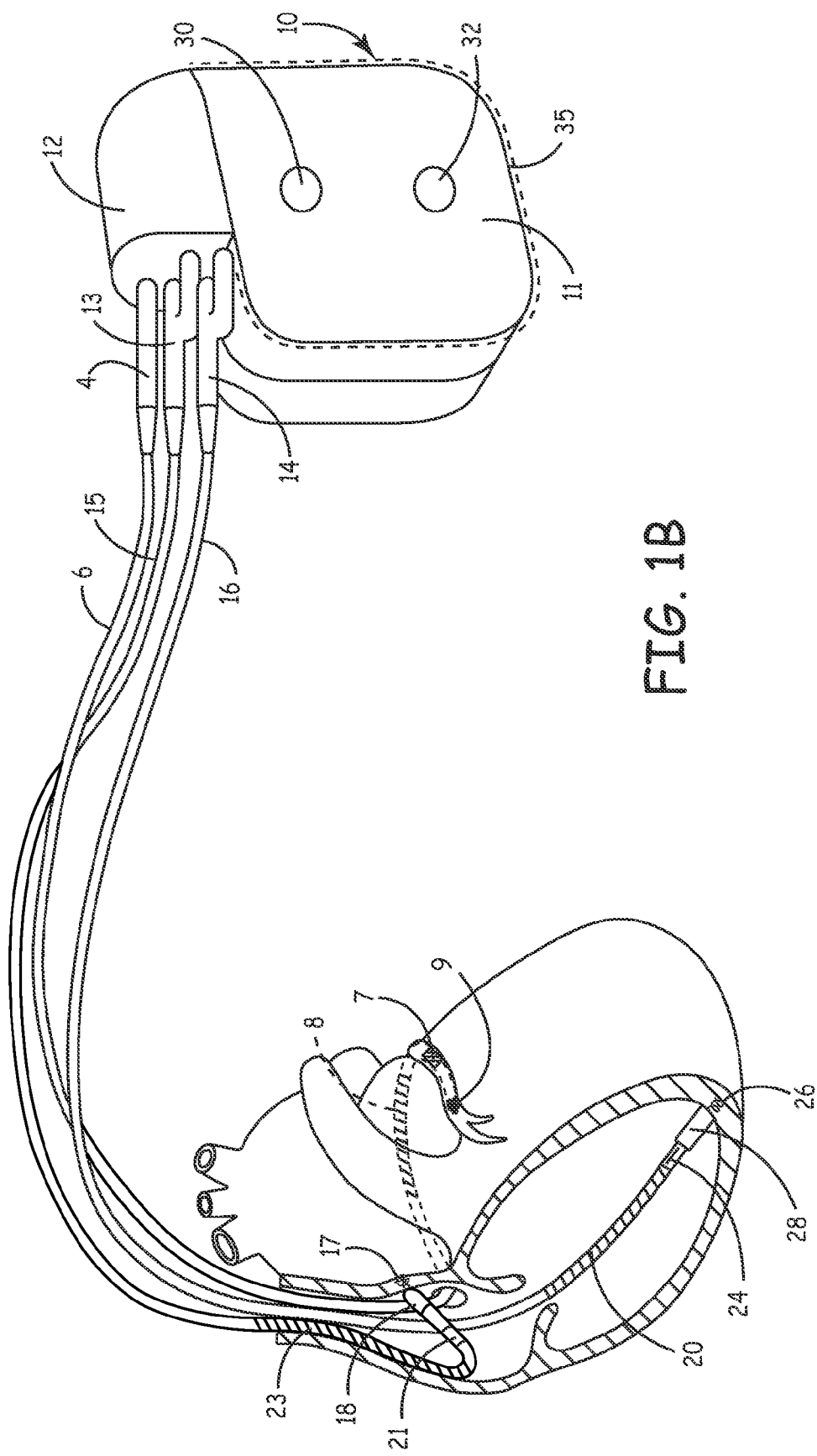
FIG. 1B is an illustration of an alternative IMD including subcutaneous ECG electrodes incorporated in the housing of the IMD.

FIG. 1B is an illustration of an alternative IMD coupled to a set of leads implanted in a patient's heart. In FIG. 1B, IMD housing 11 is provided with an insulative coating 35, covering at least a portion of housing 11, with openings 30 and 32. The uninsulated openings 30 and 32 serve as subcutaneous electrodes for sensing global ECG signals. An implantable system having electrodes for subcutanteous measurement of an ECG is generally disclosed in commonly assigned U.S. Pat. No. 5,987,352 issued to Klein, incorporated herein by reference in its entirety. In alternative embodiments, multiple subcutaneous electrodes incorporated on the device housing 11 and/or positioned on subcutaneous leads extending from IMD 10 may be used to acquire multiple subcutaneous ECG sensing vectors. Multi-electrode ECG sensing in an implantable monitor is described in U.S. Pat. No. 5,313,953 issued to Yomtov, et al., incorporated herein by reference in its entirety.

While a particular multi-chamber IMD and lead system is illustrated in FIGS. 1A and 1B, methodologies included in the present invention may be adapted for use with other single chamber, dual chamber, or multichamber IMDs that are capable of sensing and processing cardiac electrical signals and delivering electrical stimulation pulses at controlled time intervals relative to an intrinsic or paced heart rate. Such IMDs optionally include other electrical stimulation therapy delivery capabilities such as bradycardia pacing, cardiac resynchronization therapy, anti-tachycardia pacing, and preferably include arrhythmia detection and cardioversion, and/or defibrillation capabilities.

Figure 2A:
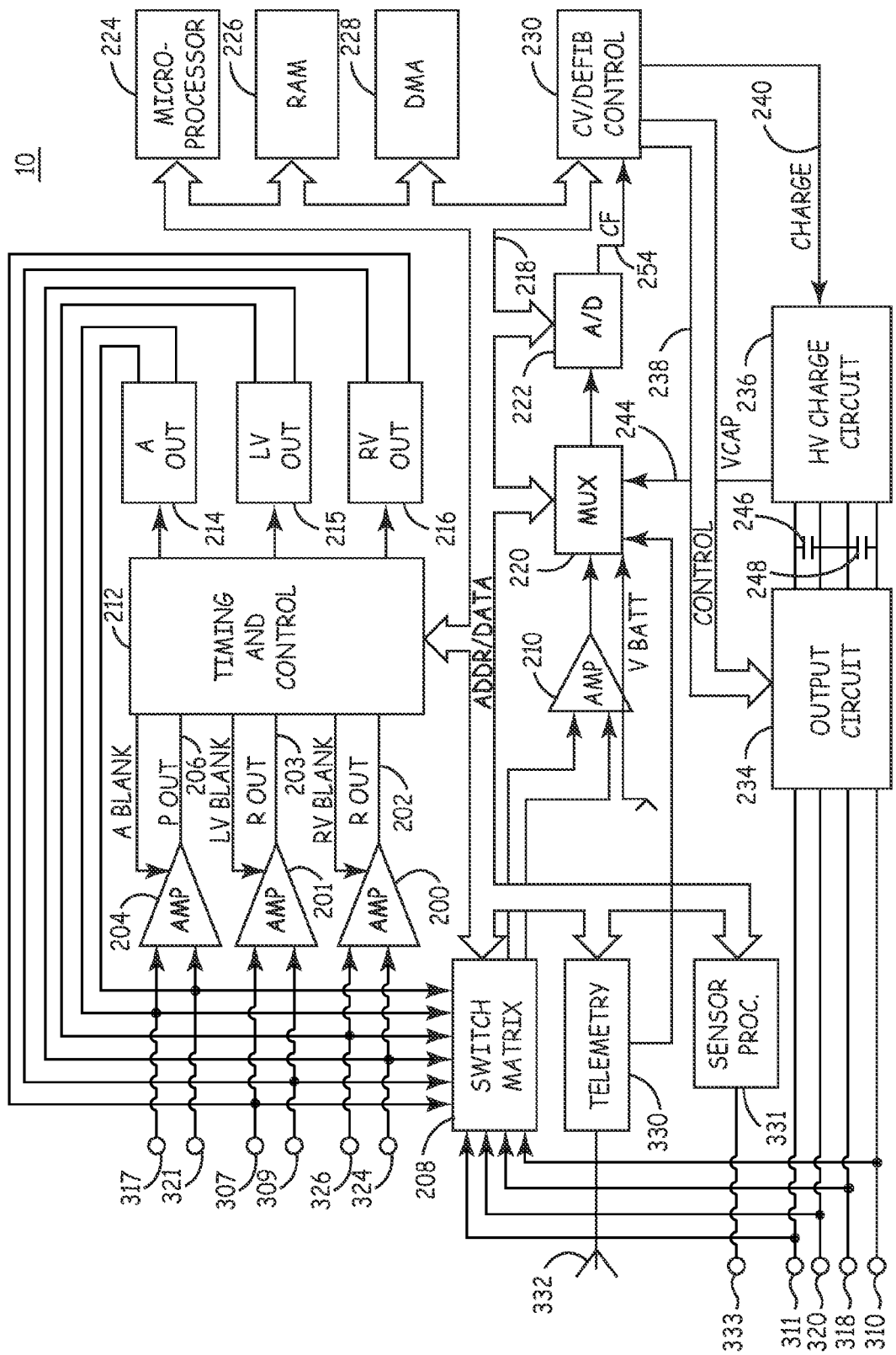
FIG. 2A is a functional schematic diagram of the implantable medical device shown in FIG. 1A.
Figure 2B:
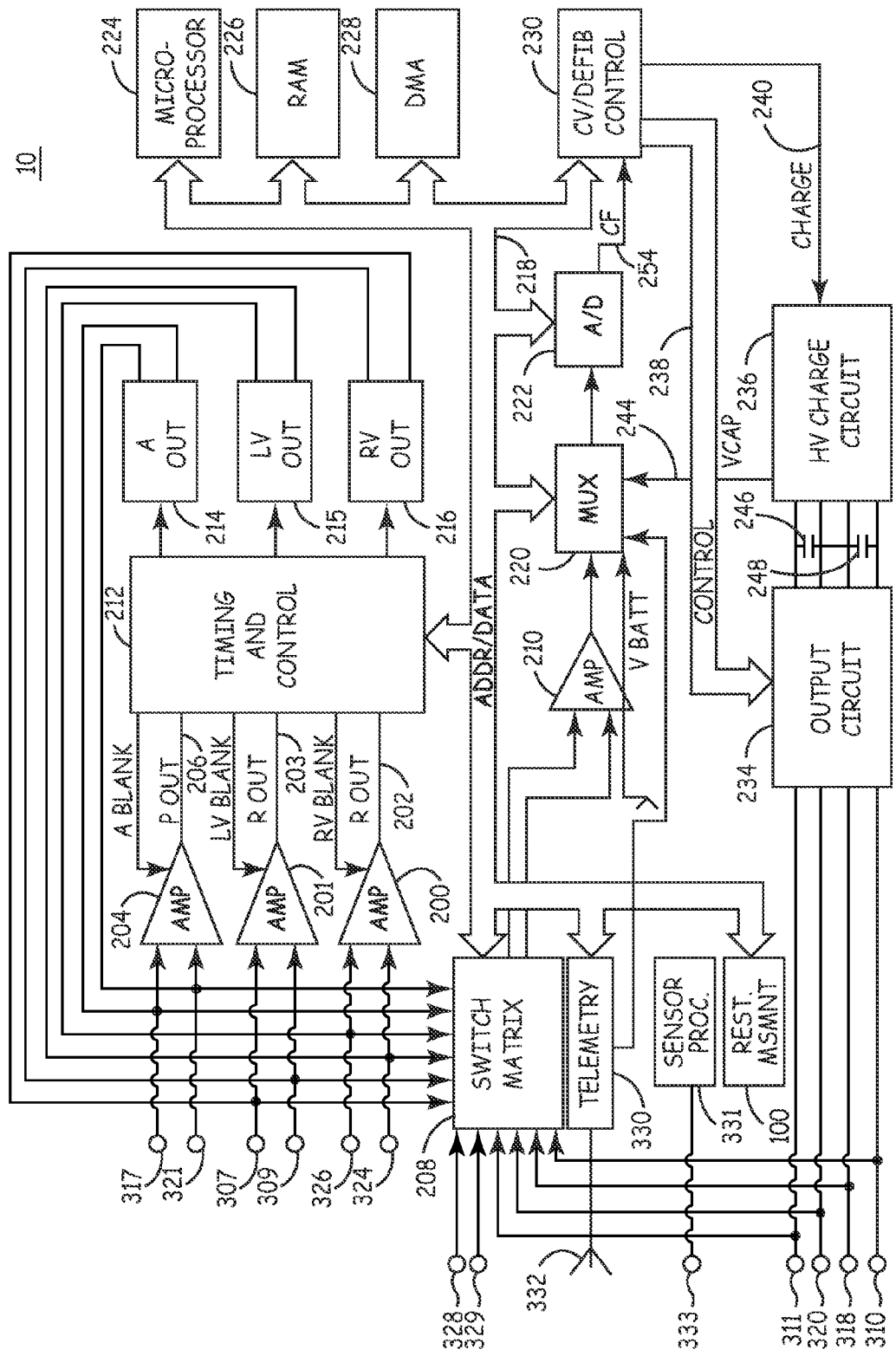
FIG. 2B is a functional schematic diagram of an alternative embodiment of the IMD, with regard to the electrode configuration of FIG. 1B, which includes dedicated circuitry for measuring electrical restitution.

A functional schematic diagram of the IMD 10 is shown in FIG. 2A. This diagram should be taken as exemplary of the type of device in which the invention may be embodied and not as limiting. The disclosed embodiment shown in FIG. 2A is a microprocessor-controlled device, but the methods of the present invention may also be practiced in other types of devices such as those employing dedicated digital circuitry.

With regard to the electrode system illustrated in FIG. 1A, the IMD 10 is provided with a number of connection terminals for achieving electrical connection to the leads 6,15,16 and their respective electrodes. The connection terminal 311 provides electrical connection to the housing 11 for use as the indifferent electrode during unipolar stimulation or sensing. The connection terminals 320,310,318 provide electrical connection to coil electrodes 20,8,23 respectively. Each of these connection terminals 311, 320,310,318 are coupled to the high voltage output circuit 234 to facilitate the delivery of high energy shocking pulses to the heart using one or more of the coil electrodes 8,20,23 and optionally the housing 11. Connection terminals 311,320,310,318 are further connected to switch matrix 208 such that the housing 11 and respective coil electrodes 20,8,23 may be selected in desired configurations for various sensing and stimulation functions of IMD 10.

The connection terminals 317,321 provide electrical connection to the tip electrode 17 and the ring electrode 21 positioned in the right atrium. The connection terminals 317,321 are further coupled to an atrial sense amplifier 204 for sensing atrial signals such as P-waves. The connection terminals 326,324 provide electrical connection to the tip electrode 26 and the ring electrode 24 positioned in the right ventricle. The connection terminals 307,309 provide electrical connection to tip electrode 9 and ring electrode 7 positioned in the coronary sinus. The connection terminals 326,324 are further coupled to a right ventricular (RV) sense amplifier 200, and connection terminals 307,309 are further coupled to a left ventricular (LV) sense amplifier 201 for sensing right and left ventricular signals, respectively.

The atrial sense amplifier 204 and the RV and LV sense amplifiers 200,201 preferably take the form of automatic gain controlled amplifiers with adjustable sensing thresholds. The general operation of RV and LV sense amplifiers 200,201 and atrial sense amplifier 204 may correspond to that disclosed in U.S. Pat. No. 5,117,824, by Keimel, et al., incorporated herein by reference in its entirety. Generally, whenever a signal received by atrial sense amplifier 204 exceeds an atrial sensing threshold, a signal is generated on output signal line 206. P-waves are typically sensed based on a P-wave sensing threshold for use in detecting an atrial rate. Whenever a signal received by RV sense amplifier 200 or LV sense amplifier 201 that exceeds an RV or LV sensing threshold, respectively, a signal is generated on the corresponding output signal line 202 or 203. R-waves are typically sensed based on an R-wave sensing threshold for use in detecting a ventricular rate.

In one embodiment of the present invention, ventricular sense amplifiers 200,201 may include separate, dedicated sense amplifiers for sensing R-waves and T-waves, each using adjustable sensing thresholds, for the detection of myocardial activity. Myocardial activity may be measured when a signal exceeding a threshold is received by an R-wave sense amplifier included in RV or LV sense amplifiers 200 or 201, causing a corresponding signal to be generated on signal line 202 or 203, respectively.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion, defibrillation and ESS functions of the IMD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art. In accordance with the present invention, digital signal analysis of a selected EGM (or subcutaneous ECG signals if available) is performed by microprocessor 224 to derive parameters related to cardiac activity and the ESS therapy pacing activity and intervals related thereto.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. Received telemetry is provided to microprocessor 224 via multiplexer 220. Numerous types of telemetry systems known for use in implantable devices may be used.

The remainder of the circuitry illustrated in FIG. 2A is an exemplary embodiment of circuitry dedicated to providing ESS, cardiac pacing, cardioversion and defibrillation therapies. The timing and control circuitry 212 includes programmable digital counters which control the basic time intervals associated with ESS, various single, dual or multi-chamber pacing modes, or anti-tachycardia pacing therapies delivered in the atria or ventricles. Timing and control circuitry 212 also determines the amplitude of the cardiac stimulation pulses under the control of microprocessor 224.

During pacing, escape interval counters within timing and control circuitry 212 are reset upon sensing of RV R-waves, LV R-waves or atrial P-waves as indicated by signals on lines 202,203,206, respectively. In accordance with the selected mode of pacing, pacing pulses are generated by atrial output circuit 214, right ventricular output circuit 216, and left ventricular output circuit 215. The escape interval counters are reset upon generation of pacing pulses, and thereby control the basic timing of cardiac pacing functions, which may include bradycardia pacing, cardiac resynchronization therapy, and anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

In accordance with the present invention, timing and control 212 further controls the delivery of extra-systolic stimuli at selected extra-systolic intervals (ESIs) following either sensed intrinsic systoles or pacing evoked systoles. The ESIs used in controlling the delivery of extra-systolic stimuli by IMD 10 are preferably automatically adjusted by IMD 10 based on measurements of electrical restitution as will be described in greater detail below. The output circuits 214,215,216 are coupled to the desired stimulation electrodes for delivering cardiac pacing therapies and ESS via switch matrix 208.

The microprocessor 224 includes associated ROM in which stored programs controlling the operation of the microprocessor 224 reside. A portion of the memory 226 may be configured as a number of recirculating buffers capable of holding a series of measured R-R or P-P intervals for analysis by the microprocessor 224 for predicting or diagnosing an arrhythmia.

In response to the detection of tachycardia, anti-tachycardia pacing (ATP) therapy can be delivered by loading a regimen from microcontroller 224 into the timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246,248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the timing and control circuitry 212 by an output circuit 234 via a control bus 238. The output circuit 234 determines the electrodes used for delivering the cardioversion or defibrillation pulse and the pulse wave shape.

In one embodiment, the implantable system may additionally include one or more physiological sensors for monitoring hemodynamic or myocardial contractile function or a metabolic status. The physiological sensor may reside within or on the heart, or endo- or extra-arterially for sensing a signal proportional to the hemodynamic function of the heart, myocardial contraction or heart wall motion, and/or a metabolic parameter. As such, IMD 10 is additionally equipped with sensor signal processing circuitry 331 coupled to a terminal 333 for receiving an analog (or, optionally a digital) sensor signal. A physiological sensor included in the implanted system may be, but is not limited to, a sensor of flow, pressure, heart sounds, wall motion, cardiac chamber volumes or metabolic parameters such as oxygen saturation or pH. Sensor signal data is transferred to microprocessor 224 via data/address bus 218 such that an index of cardiac hemodynamic or contractile performance or a metabolic status may be determined according to algorithms stored in RAM 226. Sensors and methods for determining a cardiac performance index as implemented in the previously-cited '098 patent to Bennett may also be used in conjunction with the present invention. As will be described in greater detail below, a mechanical or hemodynamic parameter of cardiac function or a metabolic parameter may be used in one embodiment of the present invention for controlling the ESI during ESS therapy delivery based on a safe and efficacious mechanical enhancement of the post-extra-systolic beats.

Figure 3:
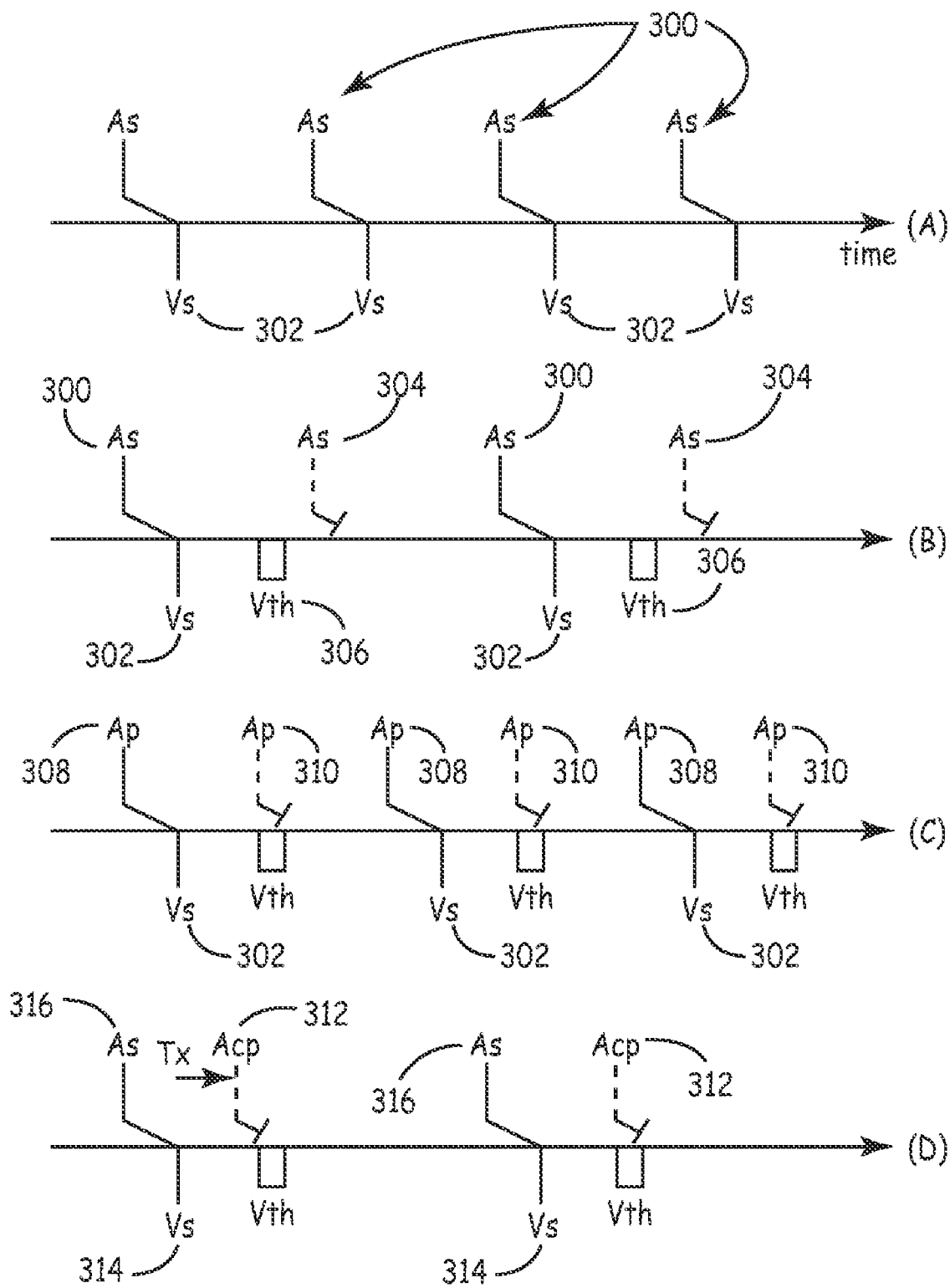
FIGS. 3-9 depict timing sequences of several cardiac cycles during which an ESS therapy is applied or modified, as applicable, according to the present invention.

FIG. 3A-D illustrates normal sinus rhythm (NSR) in FIG. 3A and various forms of ESS therapy delivery (FIGS. 3B-D) referred to herein as "atrial coordinated pacing." The following brief introduction of atrial coordinated pacing (Acp) is intended to help the reader appreciate this aspect of the present invention and, in particular, the timing sequences depicted in FIGS. 3B-D.

According to one form of Acp, electrical stimulation temporally coordinated to the occurrence of various cardiac events (e.g., standard pacing events, sensing events, Vth events, etc.) is provided to the upper and/or lower chambers of the heart. Such stimulation may be delivered both during refractory and non-refractory periods to coordinate atrial contraction, stabilize the cardiac rhythm, and optimize cardiac output. This Acp stimulation is intended to be implemented according to the present invention in a manner that minimizes the chance of inducing an arrhythmia episode.

The inventors discovered that delivery of an ESS therapy may result in intermittent AV block condition believed largely due to the extended (or additional) period of time that the ventricles remain refractory following delivery of a ventricular extra-systolic stimulation pulse (referred to as "Vth" in FIGS. 3B-D). Unfortunately, such 2:1 (A:V) conduction may produce a ventricular rate that is too slow to meet the metabolic demand of a patient, especially if based on physiologic atrial activity. In contrast, if a patient's intrinsic atrial activity produces 1:1 (A:V) conduction during ESS therapy delivery a ventricular rate can result that is too rapid for the patient. These rate fluctuations potentially offset some of the benefits provided by excitatory ESS therapy. Thus, to ameliorate these fluctuations, atrial pacing pulses can be delivered at an interval shorter than the intrinsic escape interval. In this form of Acp, the atria are AAI (or AAI/R) paced at a rate above (i.e., faster than) the intrinsic atrial rate, thus establishing a regulated 2:1 AV block while the resulting intrinsic ventricular beats occur relatively more frequently. This type of ESS therapy delivery is termed Acp through "rapid" AAI atrial pacing.

An alternative method of Acp exists wherein intrinsic or paced atrial events are followed by ventricular depolarizations (as in sinus or atrial paced rhythms) but additional stimulation pulses are provided to both the atria and ventricles at nearly the same time. This not only achieves enhanced atrial and ventricular function (via ESS therapy triggered, or "coupled," to the ventricular depolarizations) but also resets the sinus node resulting in an overall regular HR based on an intrinsic or physiologic A-A interval (i.e., interval between successive P waves) and determined by the physiologic requirements of the patient. The Acp pulse associated with this form of therapy is sometimes referred to herein as "ACP" (all capital letters) to distinguish it as a special form of atrial pacing.

The Acp and ACP concepts are best understood in reference to timing diagrams such as FIG. 3B-D. However, a first waveform (labeled "A") illustrates NSR (i.e., sinus rhythm without pacing therapy intervention). Events sensed in the atrium 300 ("As" events) conduct through the AV node to the ventricle to cause an intrinsic depolarization ("Vs" events) 302. As noted above and as depicted by a second waveform (labeled "B"), when ESS therapy delivery begins, a 2:1 AV block typically occurs. This AV block condition can oftentimes consist of an unstable form of 2:1 AV block. In the case of the second waveform (B), every other intrinsic atrial beat 304 fails to conduct to the ventricles because of the AV block condition. This AV block causes an immediate HR reduction (typically on the order of a 50% reduction) due to the fact that the extra-systole following delivery of a Vth pulse increases the refractory period of the ventricles.

Yet another waveform "C" illustrates a particular pacing embodiment for ACP (e.g., AAI pacing). According to one form of the invention, atrial pacing stimulation 303,310 occurs at a rate that is higher than the intrinsic rate. Even though 2:1 conduction is still present, the intrinsic ventricular depolarizations 302 occur more frequently because of the increased atrial rate (clearly illustrated by comparison of the relative timing of waveforms B and C).

Yet another waveform "D" can be used to illustrate another form of ACP that the inventors consider a special case of ACP. In this special case, an atrial coordinated pace 312 is delivered a relatively short time period (Tx) following a ventricular depolarization 314 or a time Ty (not depicted) following an atrial depolarization 316. Because of the AV block and the refractory state of the ventricles, this ACP paced event 312 does not conduct to the ventricles. Following this ACP paced beat 312 an intrinsic depolarization is allowed to occur in the atrium (As) 316. This intrinsic beat 316 conducts to the ventricle, resulting in a ventricular depolarization (Vs) 314. This aspect of the present invention allows, among other advantages, a patient's natural AV conduction and intrinsic rate to emerge during the cardiac cycle, providing better rate control during ESS therapy delivery. At the same time, the number of intrinsic ventricular beats occurring in a predetermined period of time is greater than would otherwise occur without any atrial pacing. This phenomenon is referred to herein as physiologic atrial coordinated pacing ("ACP"). ACP can be provided by an implantable device as illustrated herein or can be provided by trans-cutaneous pacing (TCP) stimulation timed from the surface ECG's R-wave by stimuli of sufficient amplitude to capture both atria and ventricles.

In one form of the present invention, an ESS therapy can be delivered in a DDD/R, a DDI/R and/or a VVI/R pacing modality, among others (e.g., triple-chamber bi-ventricular or resynchronization-type pacing therapies). Extra-systolic stimulation can be delivered to both the atrial and ventricular chambers (DDD/R or DDI/R modes) or to one ventricle only (VVI/R modes). An appropriate pacing mode selection can be based on a patient's bradycardia pacing indications (or lack thereof) and atrial arrhythmia status. According to one aspect of the present invention, the timing of the extra-systolic stimulation (i.e., the ESI) can be adjusted to occur earlier at higher HRs (when the refractory period of the heart is generally shorter than at lower heart rates). The extra-systolic ventricular stimulation can be monitored to assess whether or not it captured (i.e., caused a depolarization), for diagnostic purposes and/or to adjust the timing of the early stimulation. In DDD/R or DDI/R modes, ESS therapy delivery can be applied to both the atrium and the ventricle at a designated interval after a ventricular pace or sense. In VVI/R pacing modes, ESS therapy delivery can be applied to the ventricle at a designated interval after a ventricular pace event (herein "paired pacing") or after a ventricular sense (herein "coupled pacing"). Following ESS therapy delivery, the prevailing indicated pacing interval (e.g., a programmed lower rate, a mode-switch rate, a rise/fall rate, a sensor-indicated rate, etc., expressed as an interval—also known as an escape interval), is applied to the pacing cycle following cessation of delivery of an ESS therapy. In DDD/R and DDI/R modes, a short escape interval is calculated using modified A-A timing to schedule the next atrial pace: escape interval—minimum value (A-Vcp, Operating PAV). To accommodate this, any operative atrial and ventricular rate limits are defeated for a pacing cycle scheduled to deliver ESS therapy. Then, the escape intervals ending in ESS therapy delivery are discarded except that they are stored together with the pace events in an episode record buffer. Optionally, an atrial therapy pace marker is provided (e.g., counted, stored, uplinked via telemetry, etc.) for each atrial ESS therapy pace. A ventricular therapy pace marker is provided (e.g., counted, stored, uplinked via telemetry, etc.) for each ventricular ESS therapy pace. Atrial and/or ventricular supplemental markers are typically not provided (e.g., counted, stored, or uplinked) following a cycle of ESS therapy delivery.

In order to ensure that ESS therapy delivery is safe and effective, ESS therapy delivery is not applied after ventricular events that are deemed premature by the rhythm pattern. In DDD/R modes or when an atrial monitoring algorithm is enabled, an intrinsic ventricular event is considered premature if no atrial events have occurred since the last ventricular event or the atrial event occurs too close to a current event or the atrial event occurred too early in a given cardiac cycle. In DDI/R modes with such an atrial monitoring algorithm disabled, an intrinsic ventricular event is considered premature if no atrial events have occurred since the last ventricular event or the atrial event is (temporally) too near or too far from a ventricular event. In addition, a scheduled ESS therapy delivery is inhibited if an intrinsic ventricular event occurs prior to delivery of an ESS therapy pace(s). With DDD/R modes (when the atrial monitoring algorithm is enabled), scheduled ESS therapy delivery is inhibited if an atrial event occurs prior to delivery of pacing stimulus.

In addition, an interval that elapsed since an immediately prior ventricular event is compared to a minimum value (e.g., a minimum ESS therapy interval) before allowing ESS therapy delivery to occur following a ventricular event. For example, when tachycardia episode (i.e., VT/VF) detection is enabled, the interval elapsed from a detected ventricular event to an immediately previous ventricular event must be at least 30 ms longer than the longest VT/VF detection interval. For security, ESS therapy delivery is not enabled after a ventricular event if a combined count for a VT/VF detection algorithm is greater than a pre-set value (e.g., three detected sequential contractions due to a possible, or rapidly developing, tachycardia episode) or if a previously detected VT/VF episode is still in progress.

In addition, in order to preserve adequate VT/VF detection, ESS therapy delivery can be inhibited periodically. For example, after a programmable number of consecutive cycles of ESS therapy delivery, ESS therapy is not delivered. If a ventricular event detected at the start of the dropped ESS therapy delivery cycle is a pace event, the pacing interval for the dropped cycle must be at least as long as a predetermined value (e.g., a dropped interval>=a longest VT/VF detection interval+post-pace blanking+a constant, such as 30 ms). Continuing with this example, if a ventricular event is sensed at an interval less than the predetermined value (a dropped interval), an ESS therapy is not delivered during the subsequent cardiac cycle.

Further, the extra-systolic interval (ESI) can be adapted or modified based on measurements of heart rate (HR). This adaptation appears linear in the interval domain and begins adapting at a programmable rate (Start Rate) and ending at a programmable rate (Stop Rate). The amount of adaptation is also programmable. According to this aspect of the invention, at least two R-R intervals are measured and an intermediate (e.g., average, mean, median, interpolated value, etc.) value calculated. An operating ESI is then implemented based on a set percentage (or ratio) of the intermediate value. The intermediate R-R value may be updated every N cardiac cycles (wherein a lower value of N provides more rapid response to physiologic changes in HR). Other methods of deriving an ESI can be implemented such as employing a time-weighted constant with the HR metric (i.e., wherein more recent values are weighted more heavily than less recent events) and the like. As described elsewhere herein, the operating ESI should be maintained at less than half of the median R-R interval.

For capture detection of a post-extra-systolic pacing stimulus, a far-field sensing vector is preferred (e.g., a can-to-RVcoil EGM), so that capture of the ventricular ESS therapy pace (Vcp or Vth herein) can be assessed without involving same-chamber electrodes and the attendant blanking imposed thereon, the possibly confounding polarity of adjacent tissue, and to preserve operative sensing circuitry. With respect to capture detection, a capture counter is incremented if capture occurs (i.e., is positively detected), and a supplemental marker byte is provided (e.g., uplinked via telemetry) on a next ventricular event to indicate the temporal location (in the capture detection window or interval) wherein detection occurred. This capture detection mechanism can be used to periodically probe for the end of the refractory period, and, optionally, adjust the ESI to maintain a constant offset from the refractory period. For reference, a supplemental marker byte is provided (e.g., uplinked via telemetry) as a reflection of the current refractory period when ESS therapy is not delivered (e.g., for each non-therapy ventricular event).

ESS therapy delivery is preferably disabled in the event that a high voltage therapy (e.g., cardioversion or defibrillation therapy) is delivered or if a VT/VF episode is detected. Counts of atrial and ventricular capture during ESS therapy delivery are maintained during therapy delivery. When ESS therapy delivery is inhibited, a discrete counter that identifies the reason for inhibiting the ESS therapy delivery is incremented. Such counters provide a handy reference providing a reference regarding the ratio of ESS therapy delivery to other therapy (or intrinsic sinus rhythm) to a clinician and any counter that previously incremented can be cleared at any time.

According to the present invention, both high- and low-resolution trends can be collected, such as HR, ESI, and refractory period information. These trends can also be provided to a clinician and/or may be cleared at any time.

Figure 4A:
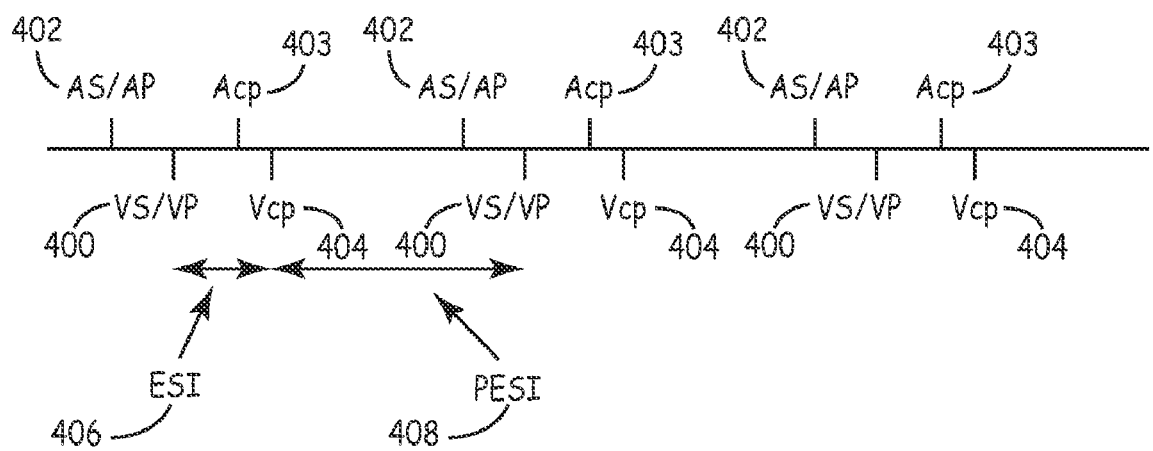
Figure 4B:
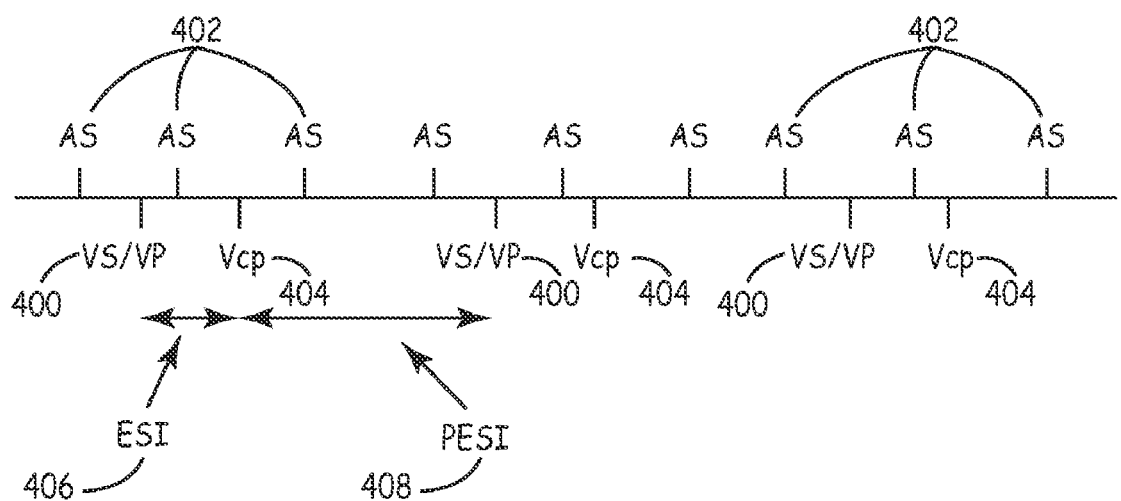

The temporal timing diagrams depicted in FIGS. 4A and 4B provide a comparison and contrast of ESS therapy delivery with (FIG. 4A) and without Acp delivery (FIG. 4B). This method of delivery is possible in VVI pacing modes, among others. In FIGS. 4A and 4B a primary ventricular event (paced or sensed) is denoted by reference numeral 400 and a primary atrial event (paced or sensed) is denoted by reference numeral 402. Also, Acp 403 refers to atrial extra-systolic pacing pulses and Vcp 404 refers to ventricular extra-systolic pacing pulses inserted to accomplish ESS therapy. An ESS therapy pacing cycle consists of an Extra-Systolic Interval (ESI) 406 and a Post Extra-Systolic Interval (PESI) 408. The ESI 406 ends when the ventricular ESS therapy pace (Vcp) 404 is delivered.

Referring now to FIG. 4A, an Acp 403 is delivered with temporal coordination to a subsequent Vcp 404. Such coordination may be accomplished by delivering the Acp at a set value decremented from the then-operative ESI. Thus, the Acp and Vcp will trigger from a primary ventricular depolarization 400. In one form of this embodiment the set value includes values of approximately 20 ms to about 40 ms, although other values may be utilized depending on a variety of factors (e.g., heart rate, activity sensor input, mechanical sensor input, metabolic sensor input, etc.). Although the range of set values may vary widely, a set value of 30 ms has shown positive empirical results.

Pacing when the HR is elevated may result in no efficacy or even worsened hemodynamics (e.g., when the temporal length of the ESI 406 is approximately equal to the PESI 408 at high rates). Such a combination of ESI 406 and PESI 408 appears to possibly be associated with an increased risk of arrthymia induction; in particular if the fast beats are part of an arrhythmia episode. For this reason, a principal ESS therapy delivery guideline involves withholding ESS therapy in the event that ESI is equal to PESI (or, stated another way delivering ESS therapy only if ESI<PESI).

An additional ESS therapy delivery guideline includes a limitation wherein ESS therapy can be delivered only if the HR is below a programmable value. The HR can be measured on a cycle-by-cycle basis from a primary ventricular event 400 to subsequent primary ventricular event 400 (or from a Vcp event 404 to the non-ESS therapy ventricular event 400 when ESS therapy is delivered).

In addition, the inventors have observed that pacing shortly after a premature beat should be more carefully considered compared to pacing shortly after a normally conducted beat. The rule described above will eliminate some premature beats, because they are "too fast." In order to further minimize the possibility of pacing shortly after a premature beat, ESS therapy can be withheld after a ventricular pace/sense event in the following situations:

1. If no non-refractory atrial event 402 occurred since a last ventricular event 400. This will eliminate situations where a premature beat occurred and may or may not have conducted retrograde and was followed by another premature event (i.e., the current ventricular event is a premature event, originating in either the atria or ventricles) and eliminate situations where the current ventricular event is premature and the last ventricular event had an accompanying far field R wave. This aspect of ESS therapy delivery guidance can also eliminate cases where the refractory atrial event conducted to produce the current ventricular event (i.e., the current ventricular event is a conducted beat), but basic pacemaker timing would typically not provide atrial tracking of this beat had it not conducted. Thus, precedent exists for not providing ESS therapy in this situation.

2. Non-refractory atrial sense 203 temporally too close to the ventricular event 400. This aspect of ESS therapy guidance eliminates situations where the current event is a premature event with a preceding far-field R wave. One current implementation of temporally "too close" includes within about 60 ms (i.e., the same interval used a typical far-field R wave rejection rule).

3. Atrial pace event 402 temporally too close to the ventricular event 400. This will eliminate situations where a current event is a premature ventricular contraction event, and a scheduled atrial pace was to occur just ahead of the premature event. A current implementation of "too close" is within about 110 ms at slower rates and within about 70 ms at faster rates (i.e., a common mechanism for determining a safety pacing interval as employed in a typical bradycardia pacemaker).

The Acp and Vcp 403,404 pulses are desirably delivered early in a given ESS therapy delivery cycle, with the intent of capturing each chamber. Thus, if a premature atrial contraction (PAC) occurs prior to delivery of an Acp 403, the Acp 403 may not capture the atria. Furthermore, the PAC wavefront could conduct to the ventricle around the time of delivery of the Vcp 404. While there are apparently no undesirable effects of the delivery of such Acp/Vcp in this case, no beneficial effects relate to such delivery. On the one hand, if the Vcp 404 captures, it may conduct retrograde and reset the sinus node. This atrial wavefront could be tracked by operative sensing circuitry and lead to a pacemaker mediated tachycardia (PMT). Another possible effect of such a sequence of events includes delivery of an atrial pace (with or without a non-competitive atrial pacing, or NCAP hold-off) because of the relatively late sinus node reset. Neither of these results are desirable. In addition, it would be desirable to withhold ESS therapy if the PAC is the start of a run of PACs or form part of an atrial tachyarrhythmia (i.e., atrial tachycardia, atrial flutter, atrial fibrillation). Therefore, if an atrial sense occurs and is determined by applicable far-field R wave criteria not to constitute a far-field R wave, ESS therapy will be withheld. If a premature ventricular contraction (PVC) occurs prior to delivery of Vcp 404, the Vcp 404 should be aborted since the heart has in effect already delivered an intrinsic extra-systolic depolarization. In addition, if the PVC occurs in an interval bounded by an Acp and a Vcp, a safety pace should be delivered.

ESS therapy delivery differs markedly from a standard single-pacing stimulus pacing modality. As a result, tachycardia detection modalities need to be modified to accommodate ESS therapy. For example, evaluation of V-V intervals is normally done on every ventricular event. Of course, ESS therapy typically (and intentionally) requires several relatively short intervals for each cardiac cycle. Such short intervals should not count towards an accumulative VT/VF detection mechanism. Otherwise, the short intervals would inappropriately bias probabilistic VF counter algorithms toward inappropriately declaring tachycardia episodes. This is a security issue from the standpoint of potential delivery of inappropriate cardioversion and/or defibrillation therapies. Therefore, ESS therapy delivery cycles that end with a Vcp 404 are ignored by the operative VT detection algorithm. That is, the V-V intervals used in the detection algorithm to compute R-R median values and determine cardiac rhythm pattern codes will start with a Vcp 404 and end at the next ventricular event 400 during ESS therapy delivery cycles. The A-A intervals used in a detection algorithm to compute P-P median values will be the most recent A-A interval at the time of a non-Vcp ventricular event (400) for ESS therapy pacing cycles. Another ESS therapy delivery option related to the foregoing involves withholding ESS therapy when an arrhythmia evidence-counting mechanism reaches a "combined count" greater than about three (as well as during a confirmed VT/VF episode).

Figure 5:
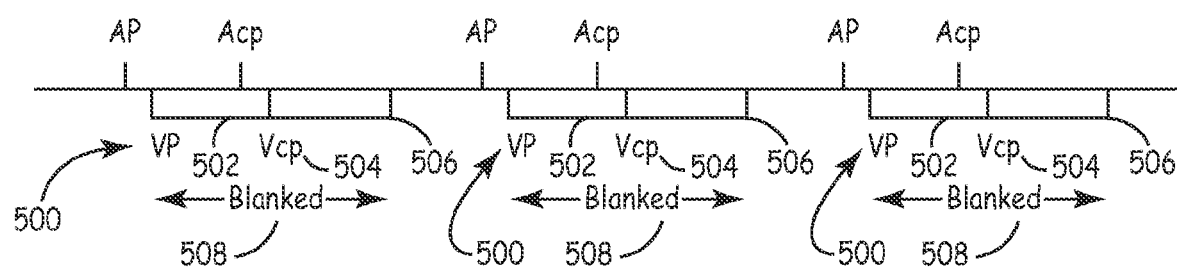

As noted above, ESS therapy presents a unique challenge to ventricular tachyarrhythmia (VT) sensing and detection, because it intentionally introduces short coupling intervals (V to Vcp) that may be less than a longest VT detection interval. As depicted in FIG. 5, ESS therapy delivery also introduces additional blanking periods 502,506 following a primary ventricular pace event 500 into a single cardiac cycle (in total such blanking is denoted by arrow 508). In a worst case, where VP blanking 502 is greater than or equal to ESI and while ESS therapy delivery occurs at an upper rate, the VT sensing window is open only about a third (~33%) of the time. For example, with VP blanking 502 of 300 ms, 300 ms of a 900 ms ESS therapy pacing cycle is available for sensing ventricular events. Thus, FIG. 5 represents a potentially worst-case example of blanking following ventricular pacing 500,504 wherein approximately 67% of the ESS therapy pacing cycle is blanked which might allows a relatively periodic VT to continue without detection.

Figure 6:
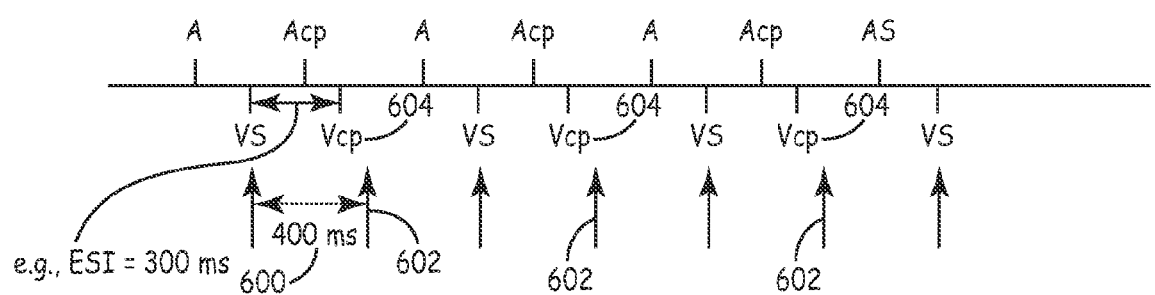

FIG. 6 shows an example of a ventricular tachycardia where every other tachyarrhythmia beat 602 occurs during a blanking period due to delivery of Vcp 604. The rhythm appears to consist of a sinus rhythm having an interval of 800 ms, when in fact the rhythm consists of a VT having an interval of 400 ms. This results from VT events 601, 602 that are sensed at half the actual rate and wherein every other VT event occurs during a blanking period. According to the present invention, one or more cardiac cycles wherein ESS therapy delivery is withheld allows detection of such VT episodes that otherwise would be effectively hidden due to the additional blanking periods introduced following delivery of a Vcp 604. The cardiac cycles wherein ESS therapy is withheld can include N cycles out of M cycles of ESS therapy delivery. If a ventricular event occurring at the start of a dropped cycle is a ventricular pacing event, the interval from Vcp to the next scheduled ventricular pace will be adjusted if necessary to ensure that it is delivered no sooner than the present Vcp blanking interval plus a maximum detection interval. If a ventricular sense occurs to end the dropped cycle, the V-V interval will be checked to ensure that it includes at least a Vcp blanking interval plus a maximum detection interval. If not, an additional ESS therapy cycle should be dropped. The escape interval following the Vcp will be set to a value normally used for pace timing, with interlocks applied to enforce the 50% sensing window and pacing withheld in the VT detection zone for the pacing cycle that starts with a Vcp. This approach offers several benefits; namely: 1) straightforward to implement within a cardiac pacing device whether implantable or external, 2) consistent with the empirical observations and theory that a patient's response to ESS therapy will be a relatively immediate lowering of HR, and 3) will preserve more of the ability to detect tachyarrhythmias quickly than would setting the escape interval based on the entire ESS therapy pacing cycle. This will be a desirable operation especially in the event that the Vcp-to-ventricular event interval more closely approximates the ventricular interval when ESS therapy is withheld for one or more cardiac cycles than does the ventricular interval associated with the "mechanical beats" (during ESS therapy delivery). Optionally, it may be desirable to have separate upper tracking rates for pacing cycles where ESS therapy is delivered and pacing cycles where ESS therapy is withheld. Such an approach allows for a higher predetermined maximum mechanical rate for ESS therapy delivery without requiring that the maximum rate during delivery of other pacing therapy to be programmed as high. For instance, with an ESI of 250 ms, then the maximum mechanical rate during ESS therapy delivery is 92 bpm with and upper tracking rate (UTR) programmed to 150 bpm. However, clinicians may not want the UTR programmed that high when ESS therapy is not being delivered so the UTR should continue as a clinician-programmable value.

Figure 7:
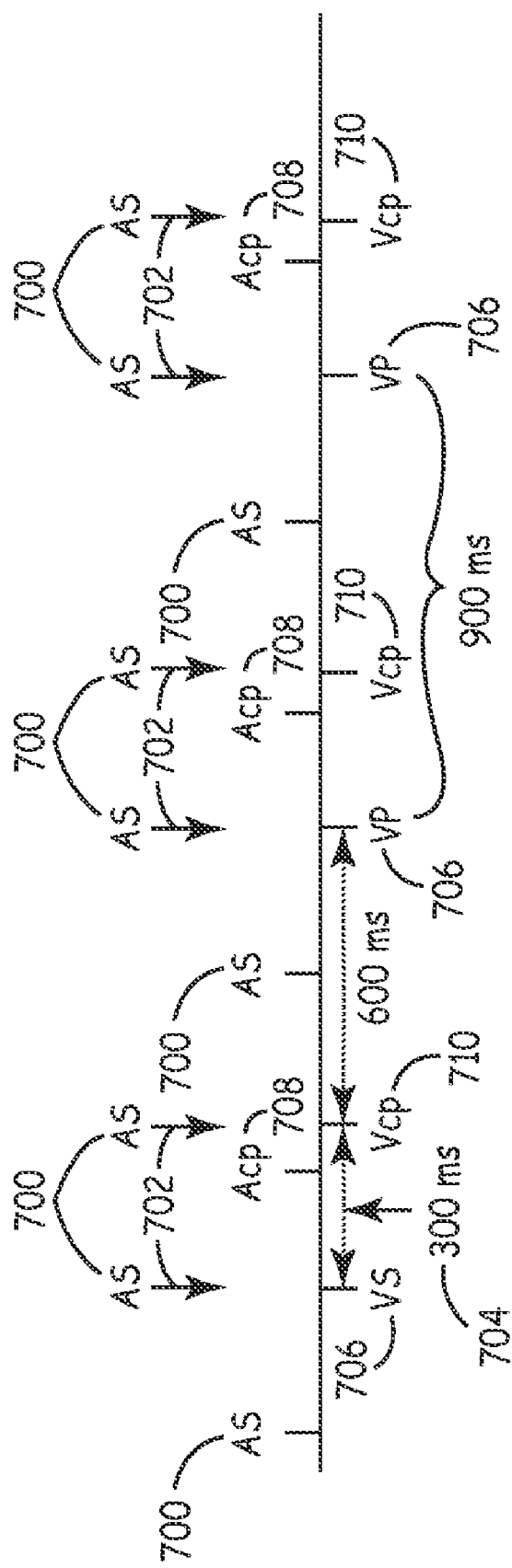

The additional blanking introduced by ESS therapy delivery also impacts the ability to detect atrial tachyarrhythmias (AT). FIG. 7 illustrates a 900 ms cardiac cycle showing an example of an atrial flutter episode characterized by relatively periodic atrial depolarizations wherein two of every three flutter waves 700 is blanked (see arrows 702). The blanking relates to blanking after a Vp 706 (optionally fixed at a predetermined value, such as 300 ms) and Acp post-pace blanking (nominally 200 ms). In this case to enhance security, the programmed sensed-AV (SAV) interval needs to be longer than typical (i.e., slightly less than the atrial flutter cycle length). FIG. 7 shows Acp delivery 708 programmed to occur a preset time prior to Vp 710. Thus, FIG. 7 depicts a form of Acp delivery wherein delivery of Acp 708 and Vcp 710 are controlled in tandem (e.g., with a fixed temporal relationship for a given HR).

Figure 8:
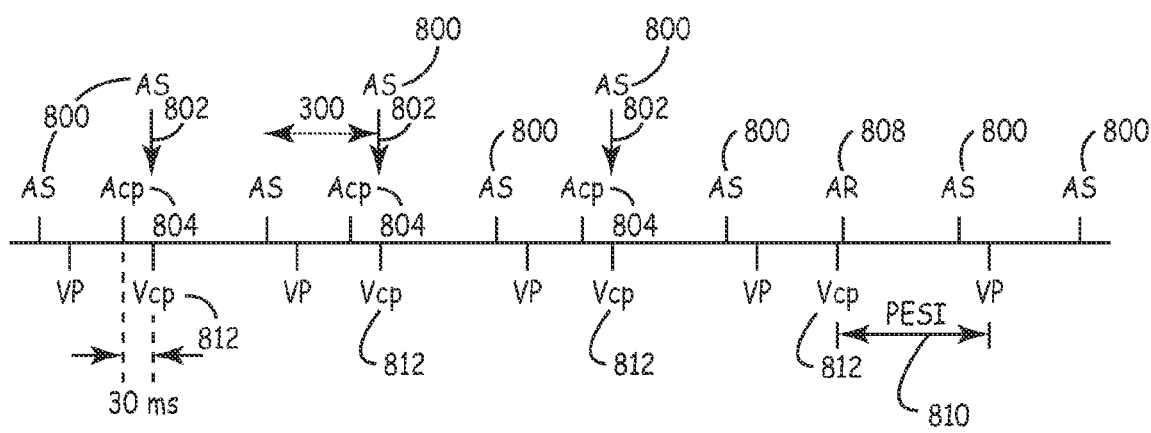

FIG. 8 illustrates an example of an atrial flutter where every other flutter wave 800 is blanked (as denoted by arrow 802) due to blanking following Acp 804. This case requires a combination of a high programmed UTR (or 2:1 conduction) and a short ESI. At the right hand side of FIG. 8, a refractory atrial event (AR) 808 occurs approximately at the same time as delivery of a Vcp 812 and during PESI 810. In order to provide adequate detection of an AT during ESS therapy delivery and perform a mode switch (e.g., suspend or modify an ESS therapy delivery mode), in the event that an refractory atrial event (AR) 808 occurs during a PESI 810. Far-field R wave criteria (e.g., using electrode pairs located outside the right ventricular chamber) can be used to determine whether "actual" atrial refractory events have occurred. In this mode of operation, ESS therapy may be suspended for three or more ventricular events. If Vcp-only (i.e., no Acp delivery) is then desired, it can be delivered until the mode switch termination criteria are met. Note that if more than one dropped cycle would be required in order for the PP Median to reflect the actual atrial cycle length.

It may be desirable to suspend delivery of ESS therapy in the event that VT/VF episodes are detected during a period of time that ESS therapy is delivered; particularly in the event that a cause-effect relationship is suspected. This suspension could occur after one or a programmable number of episodes or high voltage therapy deliveries and would offer an opportunity to modify ESS therapy parameter values before allowing ESS therapy to continue to operate. ESS therapy may be suspended after a first VT/VF detection and may be enabled or not enabled following delivery of defibrillation therapy delivery.

Figure 9:
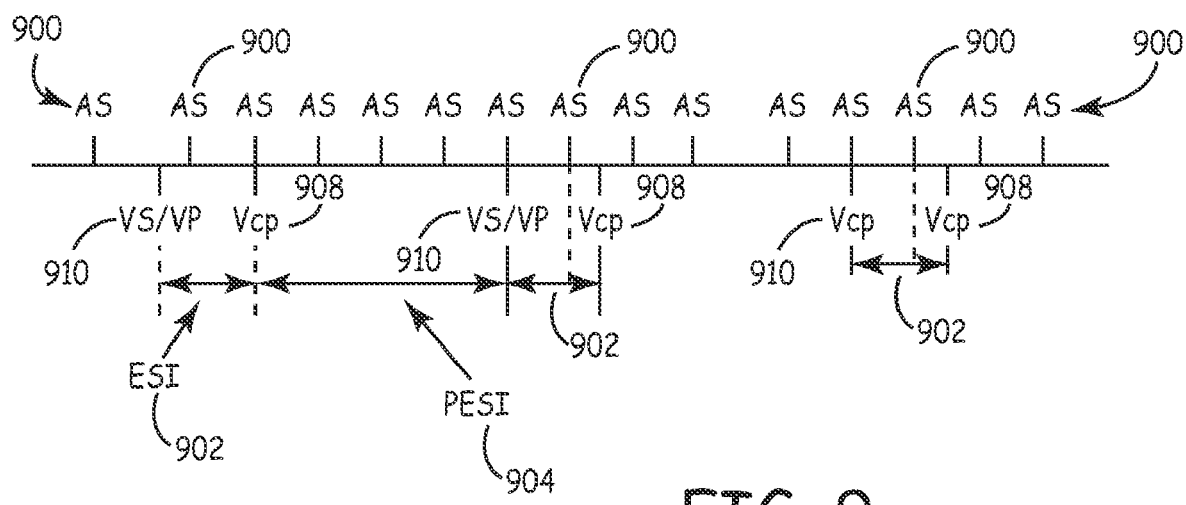

FIG. 9 illustrates ESS therapy delivery during an AT episode (a series of rapid atrial depolarizations as shown by the arrow and reference numeral 900). Assuming that ESS therapy is delivered in a VVI pacing mode or a DDI mode (or rate responsive variant thereof) a mode switch is performed. Thus, according to the present invention, in the event that an apparent AT episode 900 begins to occur (e.g., at least one unscheduled depolarization occurs in a cardiac chamber), or is detected during ESS therapy delivery, a pacing mode switch occur to a ventricular-only form of ESS therapy (Vcp 908). In addition, at any time that an atrial event is sensed during the ESI 902 (such as atrial sense event AS 906), ESS therapy delivery is modified to deliver only ventricular extra-systolic stimulation (Vcp 908). The ESS therapy delivery pacing cycle continues based only on ventricular events 910 and is still composed of an ESI 902 and a PESI 904. Another pacing mode switch may be performed from ventricular-only ESS therapy delivery to a non-ESS therapy delivery modality and/or a variety of AT suppression or AT termination techniques may be employed. In the event that the ventricular-only ESS therapy delivery modality continues the HR should continue at a relatively low value (albeit with possibly compromised hemodynamics due to a relative lack of atrial contribution to ventricular filling). In the event that a non-ESS therapy delivery modality is applied the HR can be expected to increase to approximately twice the level observed during ESS therapy delivery. In any event, any suitable technique for defeating the AT episode may be applied, such as atrial anti-tachycardia pacing (ATP), cardioversion therapy delivery and, if applicable, defibrillation therapy.

As noted, ventricular-only delivery of ESS therapy (Vcp 908) can be implemented during an episode of AT. This is desirable because an during ESS therapy delivery, especially a form of ESS therapy including atrial simulation (e.g., Acp delivery) could be expected not to capture the atrial chambers anyway but would nevertheless insert additional blanking periods. Such blanking periods may comprise a nominal interval of about 200 ms. Such blanking imposed on the atrial chamber sensing channel may interfere with the ability to monitor for termination of the AT. Thus, according to this aspect of the present invention, delivery of Acp pacing stimulus is inhibited when atrial sense events occur during the ESI 902 thus promote atrial sensing and provide for a pacing mode switch (e.g., to a ventricular-only ESS therapy delivery regime). Temporarily suppressing the Acp pacing stimulus delivery also allows atrio-ventricular ESS therapy coordination to be resumed when the AT episode terminates (e.g., by simply reinserting the Acp pacing stimulus when an atrial sense event does not occur after the AT ends).

When a patient is experiencing an AT episode, the timing of the atrial depolarizations cannot be used to discriminate premature ventricular events such as PVCs. Due at least in part to conduction-rate differences and undersensing of atrial events during an AT episode, non-refractory atrial events may or may not occur during a ventricular pacing interval (e.g., primary interval for a VP 910 or and ESI 902 for a Vcp 908). Since such non-refractory atrial events can conduct and cause a (premature) ventricular depolarization, the criteria for detecting AT episodes can be supplemented with a criterion that includes the relative pre-maturity of a ventricular sense event 910. If the ventricular event 910 is determined to occur early (as a percentage of the prevailing or then-present ventricular rate), the ESS therapy (Vcp 908) can be withheld or not initiated. Also, in the event that a PVC occurs prior to delivery of Vcp 908 (i.e., during the ESI 902), then the Vcp 908 will be withheld, at least for a then-present cardiac cycle. Furthermore, atrial arrhythmia detection techniques can be programmed to utilize or count atrial depolarizations that occur only during the PESI 904 (i.e., the interval between the Vcp 908 and the VS/VP 910) during ESS therapy delivery. Thus, if a single unscheduled atrial depolarization (of the string of atrial sense events 900) occurs during the PESI 904, a PAC or possibly the beginning of an AT episode has occurred.

As previously described, delivery of an ESS therapy should be withheld (or not initiated) in the event that a so-called "combined count" used in conjunction with an evidence accumulation-type arrthymia detection engine reaches a threshold value. One example of such an arrthymia detection engine is described in U.S. Pat. No. 5,545,186 entitled, "Prioritized Rule Based Method and Apparatus for Diagnosis and Treatment of Arrhythmias," the contents of which are incorporated by reference herein. In the context of the present invention, an exemplary threshold value of greater than three for ventricular tachycardia detection can be utilized, but other values may be employed.

In addition, for interval-based tachycardia detection engines, wherein slow ventricular tachycardia (SVT) episodes can be distinguished from tachycardia episodes occurring at higher rates based simply on the differences in the interval of time between ventricular events can be employed in conjunction with ESS therapy delivery. Thus, an SVT detection zone can be defined as a range of relatively longer intervals as compared to the intervals that form a VT detection zone. According to this aspect of the present invention, a ventricular rate limit ensures that an ESS therapy is not delivered when the observed ventricular interval was close to or in a predefined SVT or VT detection zone. In the event that an observed ventricular interval impinges upon an SVT detection zone an output signal from an activity sensor (e.g., crystal oscillator, accelerometer, etc.) or a respiration rate can be used to help determine if an apparent SVT episode is actually due to NSR (from physical exertion and the like).

In addition, by dropping one or more cardiac cycles of ESS therapy delivery, allows for a relatively unobstructed cardiac activity sensing opportunity due to relative lack of pacing and blanking compared to ESS therapy delivery. This aspect of the invention may include complete cessation of ESS therapy delivery for one or more cardiac cycles, a periodic withholding of ESS therapy and/or periodic withholding of ESS therapy. During the time that ESS therapy is not delivered another pacing modality may be applied or, for a complete lack of blanking due to pacing stimulus delivery, all pacing therapy is withheld for at least one cardiac cycle.

Thus, robust cardiac arrthymia detection testing occurs for a period of time or for several cardiac cycles. In addition to or in lieu of the foregoing, testing for the presence or emergence of an episode of ventricular arrhythmia can be implemented using an escape interval timed from Vcp 908 when ESS therapy is delivered.

Rather than suspending ESS therapy delivery in the event that a VT/VF episode is detected, ESS therapy delivery can be withheld following delivery of a cardioversion or defibrillation therapy is the episode was detected during ESS therapy delivery. Preferably, only after intervention by a clinician (e.g., interrogation of the ESS therapy delivery device) and manual re-programming of the device (either remotely or in-person) can ESS therapy delivery resume.

Thus, an implantable system and associated methods have been described for securely controlling ESS therapy delivery. The methods presented herein advantageously allow for chronic ESS therapy delivery in an implantable medical device to a patient suffering from cardiac insufficiency.

The claimed methods according to the present invention may be embodied as executable instructions stored on a computer readable medium. Said instructions cause the inventive methods to be performed under processor control. Accordingly, the present invention expressly covers all suitable processors and computer readable media, as set forth in the appended claims.

The present invention as herein described and depicted may be modified insubstantially by those of skill in the cardiac rhythm art for a given device or patient population. However, such insubstantial modifications are intended to be covered by the foregoing description as defined by the following claims.

The invention claimed is:

1. A method for managing an extra-systolic stimulation cardiac pacing therapy on a beat-by-beat basis, comprising:
    sensing electrical activity of a heart on a beat-by-beat basis to provide output signals related to at least one of: a sensed atrial depolarization, a first atrial pacing event, a second atrial pacing event, a sensed right ventricular depolarization, a first right ventricular pacing event, a second right ventricular pacing event, a sensed left ventricular depolarization, a first left ventricular pacing event, a second left ventricular pacing event;
    determining if the output signals indicate an occurrence of at least one unscheduled depolarization in a single cardiac chamber; and
    if at least one unscheduled depolarization occurred, then deciding between a mode of ceasing delivery and delivering an extra-systolic stimulation therapy to at least one chamber of the heart,
    wherein the ceasing step further comprises one of:
    withholding delivery and not initiating delivery of the extra-systolic stimulation therapy in the event that the unscheduled cardiac activity begins an accumulating tachycardia evidence counter of an on-going tachycardia episode or until such time as either the evidence counter reaches a preset threshold and a tachycardia episode is declared or the evidence counter is reset to a nominal or null value.

2. A method according to claim 1, wherein said at least one unscheduled depolarization comprises a premature atrial contraction or a premature ventricular contraction.

3. A method according to claim 1, wherein the accumulating tachycardia evidence counter collects evidence based only on ventricular events.

4. A method according to claim 3, wherein said ventricular events comprise right ventricular chamber events.

5. A method according to claim 3, wherein said ventricular events comprise right atrial chamber events.

6. A method according to claim 1, wherein the accumulating tachycardia evidence counter collects evidence based only on atrial events.

7. A method according to claim 6, further comprising:
    in the event that an atrial tachycardia is detected, switching from a currently applied pacing therapy mode to a ventricular coupled pacing therapy mode.

8. A method according to claim 1, wherein the at least one unscheduled depolarization comprises two unscheduled depolarizations.

9. A method according to claim 8, further comprising:
    searching to detect a fibrillation condition;
    in the event that the fibrillation condition is detected either:
        withholding delivery of the extra-systolic stimulation therapy, or
    not initiating delivery of the extra-systolic stimulation therapy;
    attempting to re-detect the fibrillation condition; and
    in the event that the fibrillation condition is re-detected performing at least one of:
        applying a cardioversion therapy to at least one chamber of the heart, and applying a defibrillation therapy to at least one chamber of the heart.

10. A method according to claim 9, wherein the at least one chamber of the heart comprises a ventricular chamber.

11. A method according to claim 9, further comprising:
    discontinuing delivery of the extra-systolic therapy following the application of one of the cardioversion therapy and the defibrillation therapy.

12. A method according to claim 9, wherein the attempting to detect step further comprises:
    deriving a parameter related to mechanical function of the heart; and
    comparing the parameter to a known or a derived confirmatory fibrillation condition parameter.

13. A method according to claim 12, wherein the parameter related to mechanical function comprises at least one of:
    a cardiac fluid pressure parameter, a rate of change of a cardiac fluid parameter, a mathematical integral of a cardiac fluid pressure parameter, a cardiac wall acceleration parameter, an apical acceleration parameter, a septal wall acceleration signal, a mid-basal left ventricular acceleration signal, an acoustic cardiac parameter, an impedance-based cardiac parameter.

14. A method according to claim 1, further comprising:
    initiating a non-extra-systolic stimulation pacing modality.

15. A method according to claim 14, wherein the non-extra-systolic stimulation pacing modality includes at least one of the following pacing modalities: a cardiac resynchronization pacing therapy, a single-chamber pacing therapy, a double-chamber pacing therapy, and a quadruple-chamber pacing therapy.

16. A medium according to claim 1, wherein the beat-by-beat basis comprises an extra-systolic interval and a post-extra-systolic interval and said post-extra-systolic interval exceeds said extra-systolic interval.

17. A medium according to claim 16, wherein any cardiac activity occurring during the extra-systolic interval qualifies as the at least one unscheduled depolarization.

* * * * *